(12) United States Patent
Wang et al.

(10) Patent No.: US 7,087,902 B2
(45) Date of Patent: Aug. 8, 2006

(54) FRESNEL LENS TOMOGRAPHIC IMAGING

(75) Inventors: Shaohong Wang, Troy, NY (US); Xi-Cheng Zhang, Latham, NY (US)

(73) Assignee: Rensselaer Polytechnic Institute, Troy, NY (US)

( * ) Notice: Subject to any disclaimer, the term of this patent is extended or adjusted under 35 U.S.C. 154(b) by 345 days.

(21) Appl. No.: 10/417,597

(22) Filed: Apr. 17, 2003

(65) Prior Publication Data

US 2004/0010196 A1   Jan. 15, 2004

Related U.S. Application Data

(60) Provisional application No. 60/374,199, filed on Apr. 19, 2002, provisional application No. 60/379,427, filed on May 10, 2002.

(51) Int. Cl.
*A61B 6/00* (2006.01)
*G01J 5/02* (2006.01)

(52) U.S. Cl. ............... 250/341.1; 250/340; 250/338.1

(58) Field of Classification Search ............ 250/341.1, 250/340, 338.1, 336.1

See application file for complete search history.

(56) References Cited

U.S. PATENT DOCUMENTS

| | | | |
|---|---|---|---|
| 3,815,409 A | | 6/1974 | Macovski |
| 5,952,818 A | * | 9/1999 | Zhang et al. ............ 324/96 |
| 6,057,928 A | | 5/2000 | Li et al. |
| 6,111,416 A | | 8/2000 | Zhang et al. |
| 6,242,740 B1 | * | 6/2001 | Luukanen et al. .......... 250/353 |
| 6,414,473 B1 | | 7/2002 | Zhang et al. |
| 6,556,306 B1 | | 4/2003 | Jiang et al. |
| 6,573,700 B1 | | 6/2003 | Zhang et al. |
| 6,717,668 B1 | * | 4/2004 | Treado et al. ............. 356/327 |
| 6,777,684 B1 | * | 8/2004 | Volkov et al. ............ 250/341.1 |
| 6,839,471 B1 | * | 1/2005 | Vogt, IV .................. 382/280 |
| 2001/0029436 A1 | | 10/2001 | Fukasawa |
| 2001/0038074 A1 | | 11/2001 | Zhang et al. |
| 2002/0153874 A1 | | 10/2002 | Jiang et al. |

FOREIGN PATENT DOCUMENTS

DE      199 54 900 A1    6/2001

(Continued)

OTHER PUBLICATIONS

International Search Report dated Aug. 18, 2003 to application No. PCT/US03/118388(corresponding PCT application).

(Continued)

*Primary Examiner*—Otilia Gabor
*Assistant Examiner*—Christine Sung
(74) *Attorney, Agent, or Firm*—RatnerPrestia

(57) ABSTRACT

Systems and methods for reconstructing a plurality of images of an object. An exemplary system includes a radiation source adapted to emit radiation at a plurality of frequencies; a lens with frequency-dependent focal length, such as a Fresnel lens, adapted to receive radiation modified by the object and to project onto a fixed image plane a frequency-dependent image of a slice of the object perpendicular to the radiation path; a sensor for capturing the frequency-dependent image of the object; and apparatus for facilitating creation and capture of a plurality of frequency-dependent images of the object at the plurality of frequencies. A system for reconstructing a tomographic image of the object further includes apparatus for assembling the plurality of frequency-dependent images to reconstruct the tomographic image. Methods and systems are described for use in the visible, audible, and THz frequency ranges and with broadband or narrowband radiation sources.

37 Claims, 10 Drawing Sheets

FOREIGN PATENT DOCUMENTS

WO     WO 03/042670 A1     5/2003

OTHER PUBLICATIONS

D. M. Mittleman et al.; "Recent advances in terahertz imaging"; Appl. Phys. B-68 (1999); pp. 1085-1094; USA.

Jurgen Jahns and Susan J. Walker; "Two-dimensional array of diffractive microlenses fabricated by thin film deposition"; Applied Optics; Mar. 1, 1990; pp. 931-936; vol. 29, No. 7; USA.

A. Glagolewa-Arkadiewa; "Short Electromagnetic Waves of Wave-length up to 82 Microns"; Nature; May 3, 1924; p. 640; No. 2844, vol. 113; USA.

R. Huber et al.; "How many-particle Interactions develop after ultrafast excitation of an electron-hole plasma"; Nature; Nov. 15, 2001; pp. 286-289; vol. 414; USA.

S. Wang et al.; "Characterization of T-ray binary lenses"; Optics Letters; Jul. 1, 2002; pp. 1183-1185; vol. 27, No. 13; USA.

Bradley Ferguson et al.; "T-ray computed tomography"; Optic Letters; Aug. 1, 2002; pp. 1312-1314; vol. 27, No. 15; USA.

S. Wang and X.-C. Zhang; "Tomographic imaging with a terahertz binary lens"; Applied Physics Letters; Mar. 24, 2003; pp. 1821-1823; vol. 82, No. 12; USA.

T. Dahinten et al.; "Infrared Pulses of 1 Picosecond Duration Tunable Between 4μm and 18μm"; IEEE Journal of Quantum Electronics; Jul. 7, 1993; pp. 2245-2250; vol. 29, No. 7; USA.

T. Douglas Mast et al.; "Time-domain unltrasound diffraction tomography"; 1999 IEEE Ultrasonics Symposium; pp. 1617-1620.

Salman Noach et al.; "Integrated diffractive and refractive elements for spectrum shaping"; Applied Optics; Jul. 1, 1996; pp. 3635-3639 and 5 sheets of drawings; vol. 35, No. 19; USA.

Daniel M. Mittleman et al.; "T-ray tomography"; Optical Letters; Jun. 15, 1997; pp. 904-906; vol. 22, No. 12; USA.

Zhiping Jiang, et al.; "Improvement of terahertz imaging with a dynamic subtraction technique"; Applied Optics; Jun. 10, 2000; pp. 2982-2987; vol. 39, No. 17; USA.

Q. Wu et al.; "Two-dimentional electro-optic imaging of THz beams"; Applied Physics Letters; Aug. 19, 1996; pp. 1026-1028; vol. 69, No. 8; USA.

Margaret B. Stern; "Binary Optics: A VLSI-based microoptics technology"; Elsevier Microelectric Engineering 32; 1996; pp. 369-388.

Simin Feng et al.; "Gouy shift and temporal reshaping of focused single-cycle electromagnetic pulses"; Optic Letters; Mar. 1, 1998; pp. 385-387, vol. 28, No. 5.

E. D. Walsby et al.; "Multilevel silicon diffractive optics for terahertz waves"; J. Vac. Sci. Technol. B; Nov./Dec. 2002; pp. 2780-2783; vol. 20, No. 6.

I. V. Minin, O. V. Minin; "The system of microwave radiovision of three-dimensional objects in real time"; pp. 616-619; Subsurface Sensing Technologies and Applications; Proceedings of SPIE; vol. 4129 (2000); Russia.

Igor V. Minin and Oleg V. Minin; "Fresnel Zone Plate Lens and Antennas For Millimeter Waves: History and Evolutions of Developments and Applications"; pp. 409-410; 2000 IEEE; Russia.

X.-C. Zhang; "Tomographic Imaging with Terahertz Pulses"; LEOS 2002, 15th Annual Meeting of IEEE Lasers and Electro-Optics Society; Nov. 10-14, 2002; pp. 528-529.

Eddy C. Tam et al.; "Spatial-light-modulator-based electro-optical imaging system"; Applied Optics; Feb. 10, 1992; pp. 578-590; vol. 31, No. 5.

B. Ferguson et al.; "T-ray computed tomography"; 2001 IEEE/LEOS Annual Meeting Conference Proceedings, pp. PD1.7-PD1.8, IEEE, (San Diego), 2001.

* cited by examiner

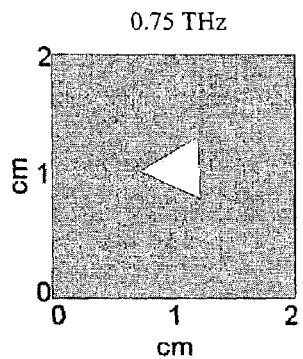
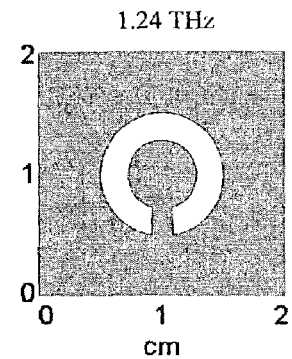
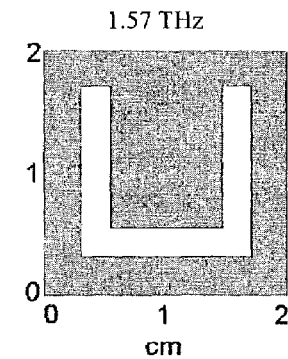
FIG. 8A                FIG. 8B                FIG. 8C
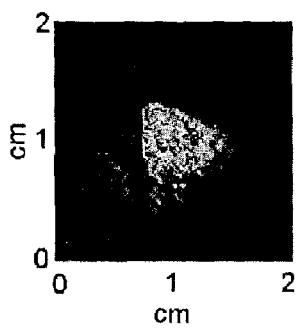
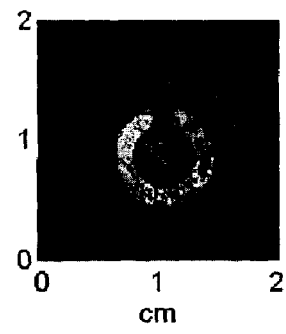
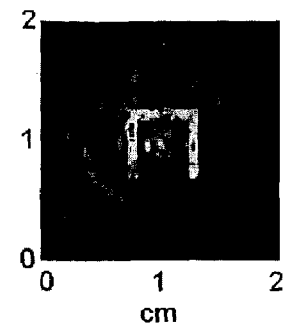
FIG. 8D                FIG. 8E                FIG. 8F

FRESNEL LENS TOMOGRAPHIC IMAGING

CROSS-REFERENCE TO RELATED APPLICATIONS

This application claims the benefit of priority to U.S. Provisional Applications Ser. No. 60/374,199, titled TOMOGRAPHIC IMAGING WITH A FRESNEL LENS, filed on Apr. 19, 2002, and Ser. No. 60/379,427, titled "Fresnel Lens Tomographic Imaging," filed on May 10, 2002, both of which are incorporated in this application by reference, along with references cited in those provisional applications.

GOVERNMENT RIGHTS

The U.S. Government has a paid-up license in the present invention and the right in limited circumstances to require the patent owner to license others on reasonable terms as provided for by the terms of contracts awarded by the U.S. Army Research Office under funding numbers DAAD199910333 and DAAD1999C0045, and by the Engineering Research Centers Program of the National Science Foundation, under award No. EEC-9986821.

TECHNICAL FIELD

The present invention relates generally to tomographic imaging and more particularly to the use of Fresnel lenses in tomographic imaging, specifically for tomographic imaging in the terahertz (THz) frequency range.

BACKGROUND OF THE INVENTION

Tomographic imaging is well-known in the art, particularly through its commercial use in the X-ray spectrum. Tomography is generally defined as any of several techniques for making a detailed image of a predetermined plane section of a solid object while blurring out the images of other planes. Computed tomography typically compiles the plane sections into a three-dimensional, computer-generated image. X-ray computed tomography has become a ubiquitous medical technique for non-invasive diagnosis of medical conditions.

Standard tomographic methods require movement of the subject to be imaged relative to the radiation source. Typically the radiation source is rotated about an axis of the subject to image slices of the object, and the object is moved along the axis to capture the desired number of image slices to be compiled to form the tomographic image.

Fresnel Binary Lenses

Conventional lenses are based on refraction, while a Fresnel binary lens (sometimes referred to simply as a "Fresnel lens" or a "binary lens") operates by diffraction. Fresnel lenses offer the ability to perform unique beam manipulation and frequency-dependant focusing.

A binary lens is a Fresnel zone plate with phase or amplitude patterns, which is formed by a series of concentric ring structures. The diffracted wave amplitude u(z) along the z-axis with the Fresnel binary lens can be written as $$u(z) = \sum_n A_n \int\int_S \exp\left[i2\pi\left(\frac{n}{r_p^2} + \frac{1}{2\lambda z}\right)(x^2+y^2)\right] dx dy \quad (1)$$

where $A_n = \text{sin } c(n/L)$, n is an integer and $L=2^M$ with M=1, 2, 3, ... $r_p^2$ is the Fresnel zone period with the area dimension, s is the area of the binary lens, and λ is the wavelength.

FIG. 1 plots the phase profile versus the square of the radius of a binary lens with the origin at the lens center point. The phase shift $\Phi(r^2)$ is a function of $r^2=x^2+y^2$. The phase shift for each step is $2\pi/L$, which corresponds to an etching depth of $\lambda/L(n_{THz}-1)$. For an 8-level silicon lens at 1 THz, the etching depth step is 15.5 μm. N is the total number of zones.

If $n/r_p^2 + 1/(2\lambda z_n) = 0$, a maximum diffraction intensity can be obtained at the focal point $z_n$:

$$z_n = -\frac{r_p^2}{2\lambda n}, n = \pm 1, \pm 2, \cdots \quad (2)$$

The diffraction efficiency η is defined as:

$$\eta = |A_{-1}|^2 = \text{sin } c^2(1/L). \quad (3)$$

As seen in Equation 3, the diffraction efficiency increases rapidly with the number of phase level L, and the calculated diffraction efficiency $\eta_{theory}$ versus L is shown in Table 1. For a binary lens with L=8, the diffraction efficiency reaches 95%, in contrast with a Al zone plate or a 2-level lens, which has 41% efficiency.

TABLE 1

|  | 2-LEVEL | 4-LEVEL | 8-LEVEL | AL ZONE PLATE |
| --- | --- | --- | --- | --- |
| $\eta_{theory}$ | 41% | 81% | 95% | 41% |

The first order focus with n=−1 is defined as the main focus with the focal length:

$$f_v = z_{-1} = \frac{r_p^2}{2\lambda} = \frac{r_p^2}{2c}v \propto v, \quad (4)$$

where c is the speed of light, and ν is the frequency of light. The focal length $f_v$ is linearly proportional to light frequency ν. FIG. 2 schematically illustrates the frequency-dependent focal length of a binary lens with an incident plane wave. Two frequencies with $v_1$ and $v_2$ are focused at the focal points with the focal length $f_1$ and $f_2$, respectively. Because $v_1 = 2v_2$, then $f_1 = 2f_2$, as calculated using Equation 4.

For a single lens imaging system with paraxial ray approximation, the relationship between object distance z, image distance z', and the focal length $f_v$ is governed by the imaging equation:

$$\frac{1}{z} + \frac{1}{z'} = \frac{1}{f_v}. \quad (5)$$

If the image plane position is fixed (therefore z' is fixed), for a wave with frequency ν, due to the frequency-dependent focal length $f_v$, the object distance z is also frequency-dependent and z has the form:

$$z = \frac{f_v z'}{z' - f_v} = \frac{r_p^2 z' v}{2cz' - r_p^2 v}. \quad (6)$$

Thus, at each frequency v, there is a corresponding value of z such that a target at location z is imaged at the position z'. Unlike with conventional refractive imaging lenses, there is no contribution of the refractive index in Equation 6. The refractive index of a binary lens introduces Fresnel loss, but does not affect the focal length or image resolution.

Terahertz (THz) Waves

The THz wave band occupies a large portion of the electromagnetic spectrum between the infrared and microwave band. Called ultra-Hertz waves in the 1920s, THz waves are an emerging frontier in imaging science and technology. Compared to the relatively well-developed medical imaging at microwave and optical frequencies, however, basic research, new initiatives, and advanced technology developments in the THz band have been limited to date. During the past decade, THz waves (also referred to as "T-ray" radiation) have been used to characterize the electronic, vibrational, and compositional properties of solid, liquid, and gas phase materials. THz waves are particularly well-suited for biomedical applications. Emerging T-ray tomographic methods are discussed in PCT Application No. PCT/US02/36279, incorporated herein by reference, titled TRANSMISSION MODE TERAHERTZ TOMOGRAPHY, filed by Rensselaer Polytechnic Institute on Nov. 13, 2002, naming Xi-Cheng Zhang, a co-inventor of the present invention, and others as inventors.

Lenses for THz Wave Systems

Lenses are a basic element in optical imaging systems. In imaging and Terahertz Time Domain Spectroscopy (THz TDS) technologies, T-ray focusing and collimating have mainly relied on parabolic mirrors, silicon lenses, and polyethylene lenses. For a broad THz beam, however, it is difficult, if not impossible, to fabricate silicon or polyethylene lenses with short focal lengths for large numerical apertures. For two-dimensional (2D), charged coupled device (CCD) THz imaging, it is very difficult to obtain a high quality THz image on a ZnTe sensor by using parabolic mirrors, due to their aberration and the difficulty of alignment. On the other hand, fabricating a 4-inch THz binary lens with a short focal length is relatively less difficult. Binary lenses are also much lighter and more compact than conventional THz optics. Despite these characteristics, binary lenses have not typically been used as THz diffraction optics for maneuvering the THz wave front.

To overcome the shortcomings of existing tomographic imaging systems and methods, a new system and method are provided. Incorporated in the system and method are the use of Fresnel lenses and the terahertz (THz) frequency range. An object of the present invention is to provide an improved tomographic imaging system and method that permit the tomographic image to be obtained without rotating or moving the target relative to the radiation source. Related objects will be evident from the summary and detailed description of the invention provided below.

SUMMARY OF THE INVENTION

To achieve these and other objects, and in view of its purposes, the present invention provides in one aspect a method for imaging an object. The method comprises aligning the following in a radiation path: a radiation source; a frequency-dependent focal length lens, such as a Fresnel lens; and a sensor for receiving the radiation as modified by at least partial transmission through or reflection from the object. The sensor is positioned to capture a frequency-dependent image projected by the frequency-dependent focal length lens onto a fixed image plane. The object to be imaged is placed in the path between the radiation source and the lens, and an nth frequency-dependent image of an nth slice of the object along a plane perpendicular to the radiation path is created using radiation at an nth frequency and captured with the sensor, for n equal to 1 through m, inclusive, where m equals an integer greater than or equal to 2. In a tomographic imaging method, a tomographic image is then reconstructed by assembling the m frequency-dependent images of the object. The imaging method may be performed at any frequency, particularly for frequencies in the THz frequency range and in the visible, audible, and microwave ranges.

In one embodiment, the method may be performed in a set of sequential steps wherein each step comprises capturing the frequency-dependent image of the object at only a narrow band of frequencies including the nth frequency. For example, a tunable filter may be placed in the radiation path between the fixed image plane and the sensor or between the radiation source and the object. A tunable radiation source may also or instead be used.

In one embodiment, the radiation source may comprise a broadband THz radiation source and the method may comprise illuminating the object with a broadband THz pulse over a series of time delays between the broadband THz pulse and an optical probe pulse. A temporal waveform of the broadband THz pulse transmitted through the object is captured at a plurality of pixels on the fixed image plane, and a Fourier transform of each temporal waveform is taken to provide a THz field amplitude distribution for each of the m frequencies. In such an embodiment, the THz field amplitude distribution comprises the frequency-dependent image for each of the m frequencies.

Another aspect of the invention is a system for reconstructing a plurality of images of an object, the system comprising: a radiation source adapted to emit radiation at a plurality of frequencies in a radiation path directed at the object; a frequency-dependent focal length lens, such as a Fresnel lens, adapted to receive radiation modified by the object and to project onto a fixed image plane a frequency-dependent image of a slice of the object perpendicular to the radiation path; a sensor for capturing the frequency-dependent image of the object; and apparatus for facilitating creation and capture of a plurality of frequency-dependent images of the object at a plurality of frequencies. A tomographic imaging system further comprises a mechanism for assembling the plurality of frequency-dependent images of the object to reconstruct the tomographic image of the object.

In one exemplary embodiment, the apparatus for facilitating creation and capture of a plurality of frequency-dependent images comprises a broadband radiation source and a tunable filter placed in the radiation path, for example between the radiation source and the object or between the fixed image plane and the sensor. In particular, where the radiation source comprises a white light source, the tunable filter may comprise an electrically tunable filter such as a liquid crystal tunable filter, an acoustic-optical tunable filter, or an interferometer or spectrometer, such as a Fabry-Perot Etalon. In one embodiment, the apparatus for facilitating creation and capture of a plurality of frequency-dependent images may comprise a tunable radiation source.

In another embodiment, the radiation source may comprise a broadband THz radiation source, in which case the system may further comprise a source for generating an optical beam, a splitter for splitting the optical beam into a pulse beam and a probe beam, a delay stage for generating a series of time delays between the pulse beam and a probe beam, an electro-optic (EO) emitter for converting the optical pump pulse into a THz pulse, and an EO sensor for modulating the probe beam with the THz pulse as modified by the object. The system further comprises a device for capturing the modulated probe pulse at a plurality of pixels on the fixed image plane at a plurality of delay times between the pump pulse and the probe pulse to enable characterization of a complete temporal waveform for the THz pulse for each pixel. The system also comprises a processor for taking a Fourier transform of each temporal waveform to provide a THz field amplitude distribution for each of the plurality of frequencies. The THz field amplitude distribution comprises the frequency-dependent image for each of the plurality of frequencies.

It is to be understood that both the foregoing general description and the following detailed description are exemplary, but are not restrictive, of the invention.

BRIEF DESCRIPTION OF THE DRAWING

The invention is best understood from the following detailed description when read in connection with the accompanying drawing. It is emphasized that, according to common practice, the various features of the drawing are not to scale. On the contrary, the dimensions of the various features are arbitrarily expanded or reduced for clarity. Included in the drawing are the following figures:

FIGS. 8A–8F depict the patterned plastic sheets OT, OC, and OU and the inverted tomography images of the patterned plastic sheets as captured by the system depicted in FIG. 7;

DETAILED DESCRIPTION OF THE INVENTION

Figure 1:
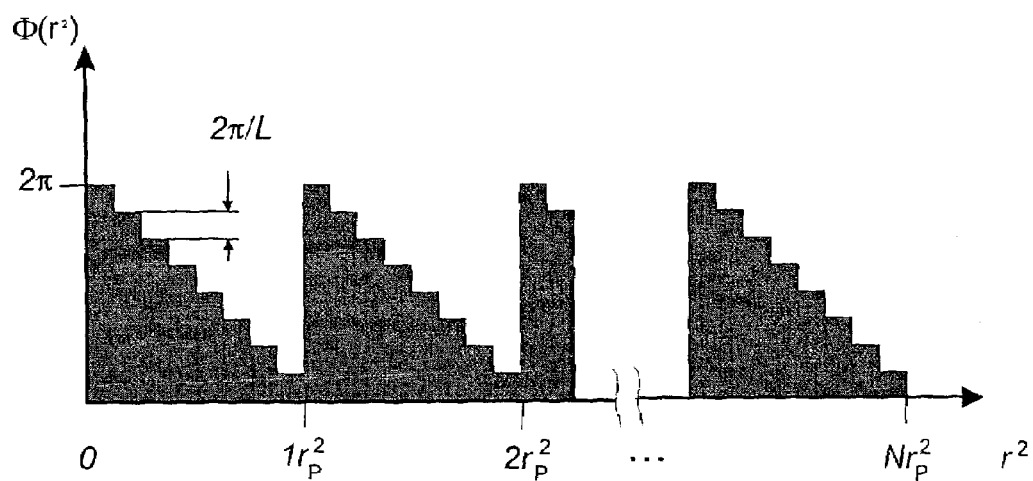
FIG. 1 is a schematic illustration plotting the phase profile of the square of the radius of a circular multi-phase-shift binary lens.
Figure 2:
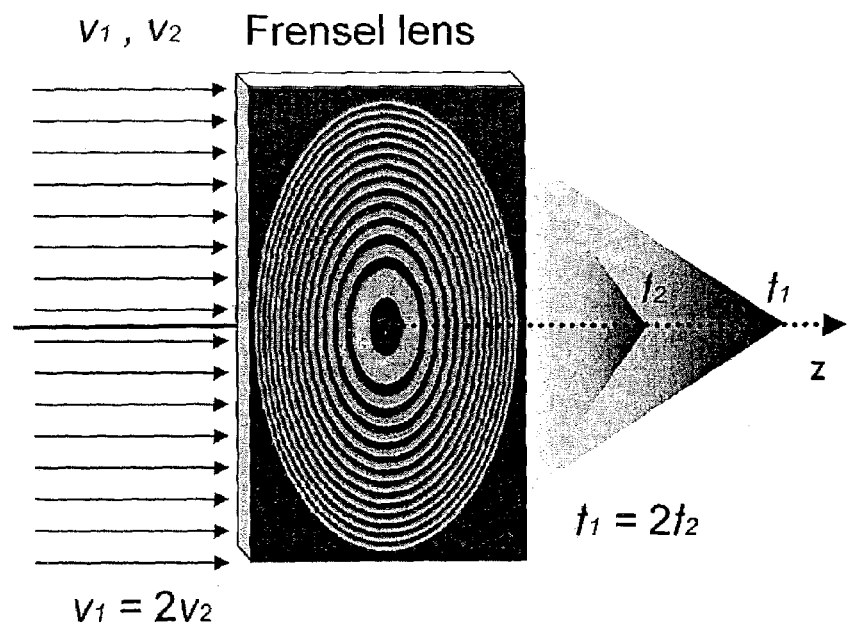
FIG. 2 is a schematic illustration of the frequency-dependent focal length of a Fresnel lens.

The linearly frequency-dependent focal length of a Fresnel lens allows tomographic imaging of a target using multiple frequencies. Objects at various locations along the beam propagation path may be uniquely imaged on the same imaging plane by using a Fresnel lens and varying the frequency of the imaging beam. At each frequency, a Fresnel lens images a different plane section of a target object while images from other depths remain blurred. This procedure allows the reconstruction of an object's tomographic contrast image by assembling the frequency-dependent images, providing a new tomographic imaging modality. Unlike other tomography methods, which typically require the rotation of the target relative to the radiation source, the tomographic image using a Fresnel lens may be obtained without rotating or moving the target relative to the radiation source.

Extraction of a Sectional Image

The tomographic imaging system described herein is valid for weak scattering targets. When a THz wave propagates through such a target, the scattered THz wave can be described by the first-order Born or Rytov approximation, as explained by A. Kak and M. Slaney, *Principles of Computerized Tomographic Imaging* (Society of Industrial and Applied Mathematics, Philadelphia, 2001), incorporated herein by reference. Under this assumption, if an object, described by an object function $o(x_o, y_o, z_o)$, has a finite thickness, then each of the vertical thin sections in this thick object at a given z produces an image in the image plane at z'. The total field in the image plane at z' is the superposition of the contributions from each section and can be written as:

$$|U_i(x_i, y_i, z')| \propto \left| \int\int\int o(x_o, y_o, z_0) \exp[ik(z_o - z')] \right.$$
$$\left. h(x_o + Mx_i, y_o + My_i, z_o - M^2 z') dx_o dy_o dz_o \right| \quad (7)$$

where $U_i(x_i, y_i, z')$ is the image plane field distribution, $M = -z'/z$ is the magnification factor, and the Fourier transform of $h(x,y,z)$ is the THz imaging system's three-dimensional coherent transfer function, which can be determined by an imaging system characterization procedure such as disclosed by M. Gu, *Principles of Three-Dimensional Imaging in Confocal Microscopes* (World Scientific, New Jersey, 1996), incorporated herein by reference. The z' and z satisfy Equation 5. The net contribution from the section $o(x_o, y_o, z)$ can be calculated according to Equation 7. The accuracy of such calculation depends, however, on the signal-to-noise ratio (SNR) of the imaging system and the accuracy of the first Born approximation.

Imaging Using Binary Lenses

Fresnel lens tomographic (FLT) imaging using binary lenses is particularly well suited for use with broadband terahertz (THz) wave pulses and tunable narrowband imaging beams. From a practical standpoint, a "narrowband" wave is typically a wave having a frequency bandwidth much smaller than the center frequency of the wave, whereas a "broadband" wave is typically a wave having a frequency bandwidth comparable to or larger than the center frequency of the wave. Tomographic imaging with binary lenses may also be applied to other frequency ranges, however, including but not limited to microwave, visible, and acoustic spectra. In fact, FLT imaging can be applied to any electromagnetic wave governed by the Lens Law (1/o+ 1/i=1/f, where o is the object distance, i is the image distance, and f is the focal length).

Figure 3:
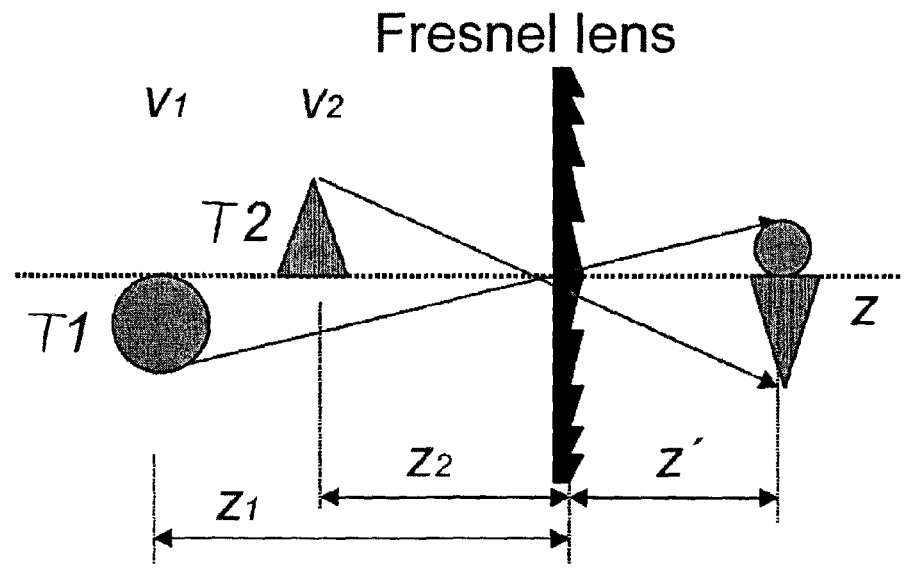
FIG. 3 is a schematic illustration of how targets at different locations can be focused on the same fixed image plane using a Fresnel lens at different frequencies for each target.

FIG. 3 shows an exemplary tomographic imaging arrangement using multiple (n) targets T1 and Tn (n=2 as shown in FIG. 3) at different locations. The multiple targets may be imaged at the same fixed image plane (FIP) using corresponding frequencies ν that satisfy Equation 6. Each point in the $z=z_1$ or $z=z_2$ plane is imaged onto a corresponding point on the z' plane with the magnification factor $-z'/z$ at the frequency $v_1$ and $v_2$.

Figure 4:
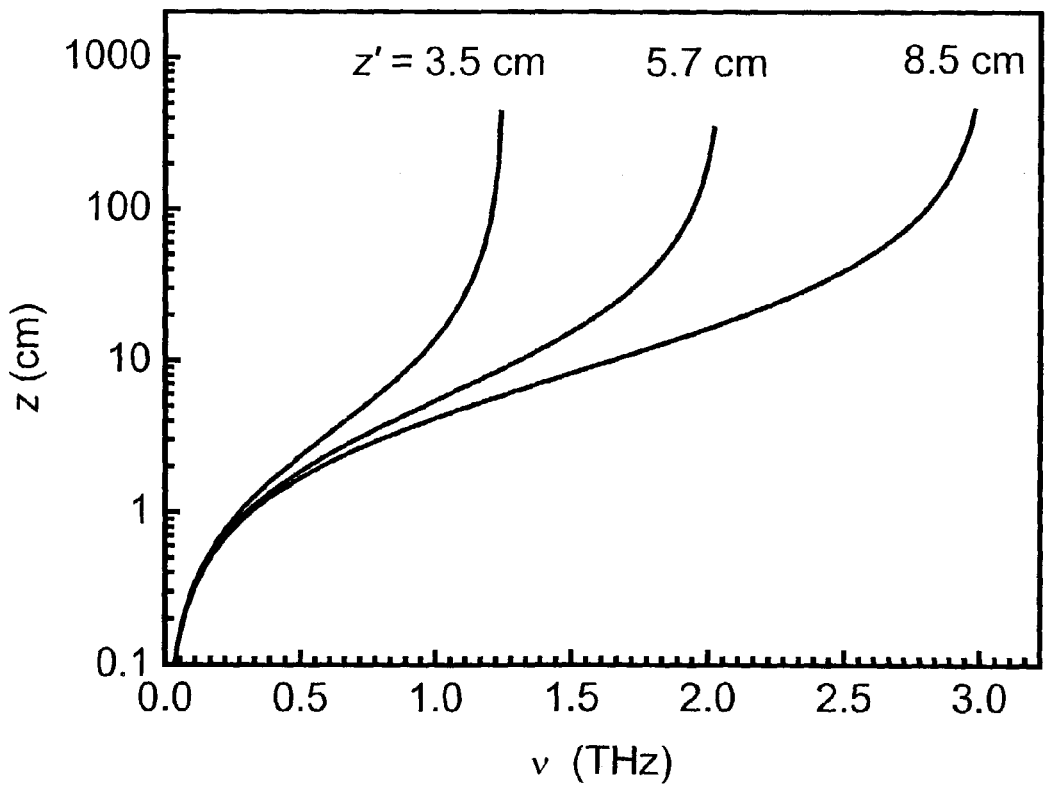
FIG. 4 is a plot of calculated curves of the object distance z versus the imaging beam frequency ν with the imaging distance z' at 3.5 cm, 5.7 cm, and 8.5 cm, respectively, using a Fresnel lens having a focal length f of 2.8 cm at 1 THz.

FIG. 4 depicts a plot of calculated z versus the imaging beam frequency ν with three different imaging distances z' at 3.5 cm, 5.7 cm, and 8.5 cm, respectively, using a Fresnel lens with a focal length f of 2.8 cm at 1 THz. From FIG. 4 it can be seen that an imaging range in excess of one meter can be achieved using imaging frequencies up to 3 THz.

Unlike other terahertz wave imaging methods (such as time-of-flight, or conventional T-ray tomography), which may provide spatially resolved spectroscopic information, a limitation of using a Fresnel lens is that the image only contains the contrast image along the z-axis without spectroscopic information. Several factors may limit the resolution of the reconstructed tomographic image along the z-axis, which is defined as the depth resolution. These factors include the depth uncertainty along the z-axis induced by frequency uncertainty and by the depth of focus, and the caustic curve induced by the nonparaxial ray.

Depth uncertainty Δz along the z-axis induced by frequency uncertainty can be estimated by differentiating Equation 6 to obtain:

$$\Delta z = \left(\frac{z^2}{f_v}\right)\frac{\Delta v}{v}. \quad (8)$$

For a broadband THz system with a frequency resolution of Δν=1 GHz and ν=1 THz, from Equation 8, the depth uncertainty Δz=0.6 mm. For a narrowband THz source with Δν<1 MHz, the depth resolution Δz=0.6 μm.

Depth uncertainty Δz along the z-axis induced by the THz beam depth of focus has the largest effect on the depth resolution and is defined as twice the Rayleigh range of the THz beam on the image plane. The measured depth of focus at 1 THz is 3 mm. Because the depth uncertainty of the target position is equal to the depth of focus divided by the square of the magnification factor, the uncertainty of the target position is a function of z. Thus, the depth resolution decreases for a large value of z.

Several methods may be employed to improve the depth resolution depending on which of the above factors is most limiting. Where depth of focus limits the resolution, one can use a longer imaging distance z' at the expense of spatial resolution in the x-y plane, or use a larger numerical aperture binary lens. When the frequency resolution limits the depth resolution, it can be improved by increasing the frequency measurement resolution, for instance, by extending the observing time window.

Due to the diffractive nature of the Fresnel imaging lens, tomographic imaging using a Fresnel lens is more sensitive to the imaginary part (absorption) of the dielectric constant distribution than to the real part (refractive index) of the dielectric constant.

Targets for use in FLT imaging are preferably essentially transparent to the type of radiation being used and the scattering of the beam by the target is preferably small enough so that the scattering of the layer near the lens does not "erase" the image of the layer far away from the lens.

Fabrication and Characterization of Binary Lenses

Figure 5:
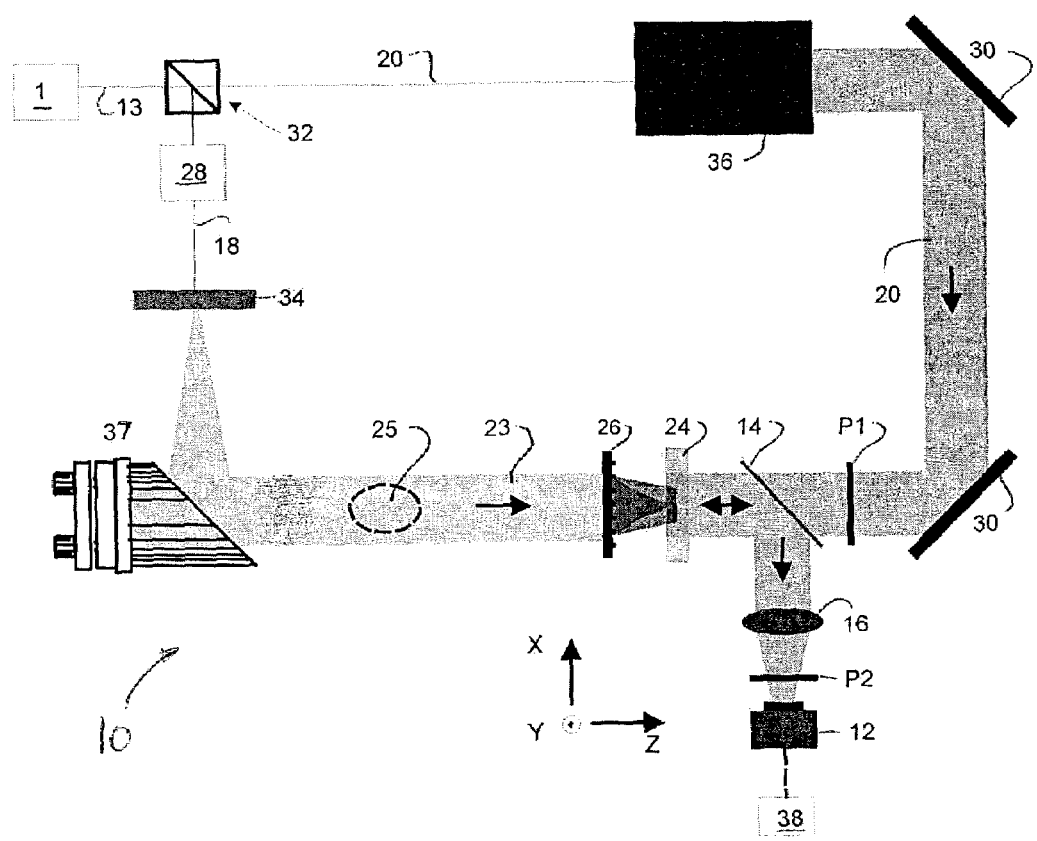
FIG. 5 is a schematic illustration of an exemplary broadband imaging system used for characterization of binary lenses and for imaging objects.

FIG. 5 schematically illustrates an exemplary EO imaging setup 10 with a CCD camera 12. The use of CCD cameras for two-dimensional imaging is discussed generally by Wu, Hewitt, and Zhang, in "Two-dimensional electro-optic imaging of THz beams," *Appl. Phys. Lett.* 69 (8) pp. 1026–1028 (1996), incorporated herein by reference. A laser 1 (such as a 1-kHz repetition rate, amplified, Ti:sapphire laser capable of generating 100 fs pulses with energy of 700 μJ) (creates a laser beam 13, which is split into a pump beam 18 and a probe beam 20. Both probe beam 20 and pump beam 18 may be expanded to 2.5 cm (1/e) and collimated. For example, FIG. 5 depicts pump beam 18 being expanded by an emitter 34 and collimated with a parabolic mirror 37, whereas probe beam 20 is expanded by an expander 36.

Pump beam 18 is directed through emitter 34, such as a 3 mm thick <110> ZnTe emitter, which generates a THz pulse 23 via optical rectification. The 2D THz image formed on the fixed image plane (FIP) is captured by an EO sensor 24, such as a 4 mm thick <110> ZnTe crystal with an effective aperture of 2 cm, which encodes the image onto probe beam 20 via the EO effect, as is well-known in the art. The image carried by the encoded probe beam 20 is focused onto CCD camera 12, which is connected to a processor/memory device 38, such as a computer, which stores and processes data collected by CCD camera 12.

The probe beam reflected from EO sensor 24 may be focused onto CCD camera 12 via a pellicle 14, a lens 16, and a polarizer P2. A polarizer P1 is also provided. The polarization directions of polarizers P1 and P2 are perpendicular to each other. For purposes of imaging set-up 10 shown in FIG. 5, the coordinate system is as follows: the axis of binary lens 26 is the Z-axis, the X-axis is parallel to an optical table (not shown), and the Y-axis is perpendicular to the optical table.

By scanning the time delay, as created by a delay stage 28, between THz pulse 23 and probe beam 20, and by moving binary lens 26 along the Z-axis, the spatial and temporal THz distribution for binary lens 26 can be determined. Although shown with delay stage 28 on pump beam 18, delay stage 28 may instead be on probe beam 20, as is known in the art. Although shown schematically with various optics, including mirrors 30 and 37, beam splitter 32, expander 36, lens 16, pellicle 14, and polarizers P1 and P2, positioned to direct the depicted beams in a manner that produces a logical depiction in FIG. 5, it should be understood that systems comprising any combination of optics, including but not limited to mirrors, splitters, polarizers, expanders, collimators, lenses, pellicles and the like, or the absence thereof, may be used and positioned as needed to fit the physical layout and desired purposes of the system, as is well-known in the art.

Binary lenses may be manufactured by any method known in the art. Exemplary 2-level, 4-level, and 8-level lenses with a 30 mm diameter and having a total of 14 zones, with a focal length of 25 mm at 1 THz, have been fabricated on silicon wafers by ion etching, by methods known in the art and as described, for example, in E. Walsby, R. Cheung, R. Blaikie and D. Cumming, "Fabrication of multilevel silicon diffractive lenses for terahertz frequencies," Proc. SPIE, Vol. 79, 3879 (1999), incorporated herein by reference. Silicon has a nearly frequency-independent refractive index of 3.42 in the far infrared region from 0.5 to 2 THz. Accordingly, the required etch depth, $\lambda/[L(n_{THz}-1)]$, is small, facilitating fabrication of thin binary lenses.

The focused THz intensity increases with the number of levels in the T-ray binary lenses. Also, a smaller focal area and sharper focused THz peak are observed as the number of levels in the binary lens increases. This corresponds to the enhanced diffraction efficiency, which increases dramatically with the number of levels of binary lenses. As the number of levels of the binary lenses increases, the measured diffraction efficiency approaches the theoretical value. This result is in accordance with the rule of thumb that, as the binary level increases, the binary lens is more tolerant to fabrication errors.

Figure 6:
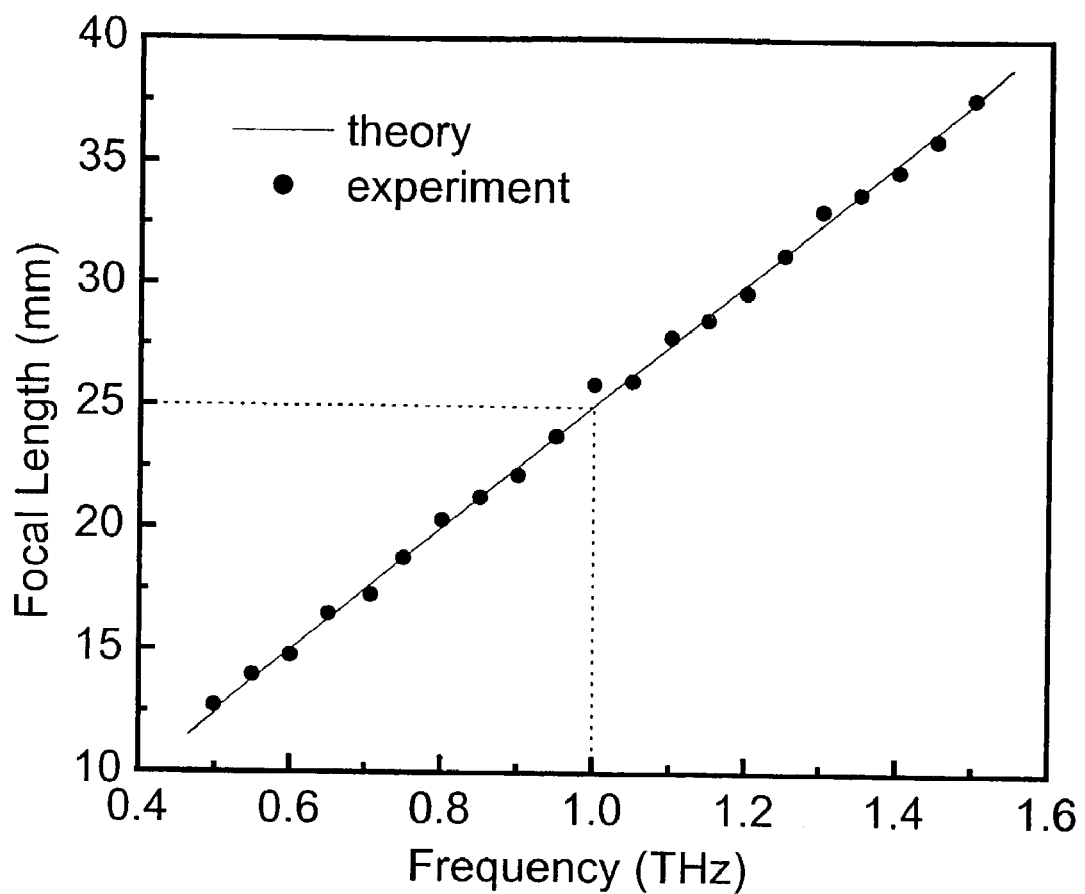
FIG. 6 is a plot of the variation of THz focal length with THz frequency for an 8-level T-ray binary lens, showing the calculated result as a line, and measured experimental data as solid circles.

The frequency-dependent response of a binary lens may be determined by performing a Fourier transformation of measured THz pulses. The focal length of the binary lens at each frequency may be determined by finding the lens-detector separation that results in the maximum THz intensity. As shown in FIG. 6 for an exemplary 8-level T-ray binary lens as described above, the focal length increases with the THz frequency. FIG. 6 confirms that the experimental results are well fitted by the theoretical curve, showing that the T-ray binary lens has a focal length of 25 mm at 1 THz as designed. Less aberration was observed on the binary lens as compared with a polyethylene lens.

Diffractive binary lenses can be used for both narrowband and broadband THz applications. The unique properties of binary lenses, such as flexibility in design, capability of integration, and relatively more freedom in choosing the substrate, make it possible to fabricate excellent optics for narrowband THz wave imaging and sensing applications.

The following examples are included to more clearly demonstrate the overall nature of the invention. These examples are exemplary, not restrictive, of the invention.

EXAMPLES

Example 1

Figure 12A:
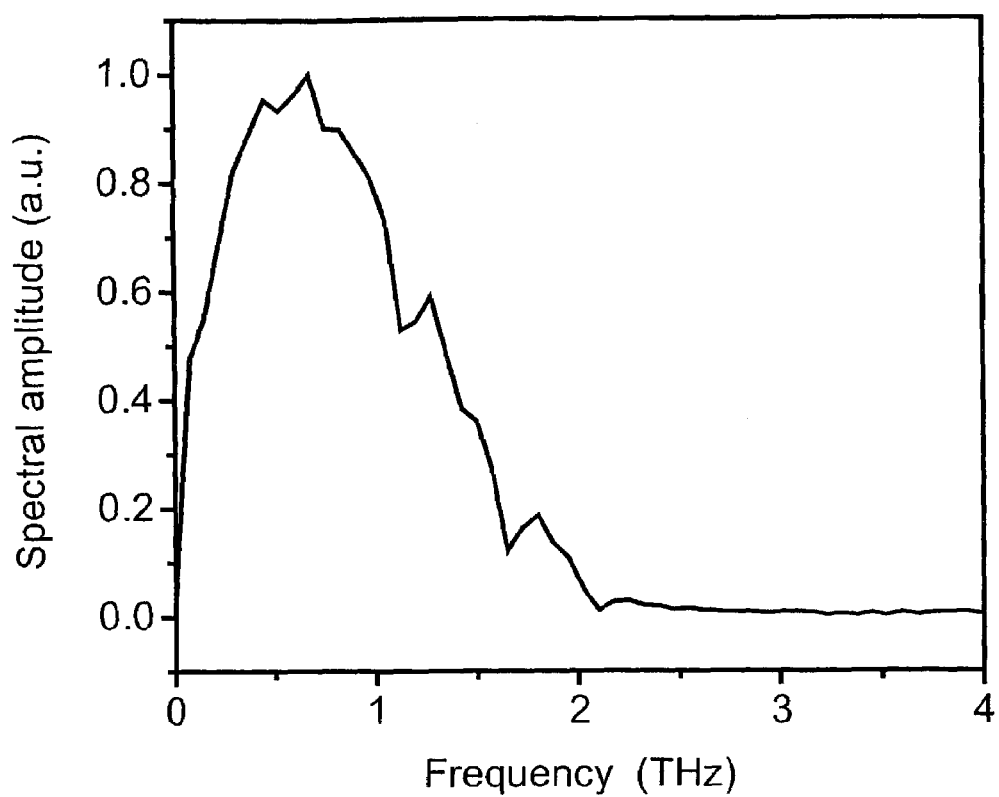
FIG. 12A shows a Fourier spectrum of an exemplary broadband THz pulse.
Figure 12B:
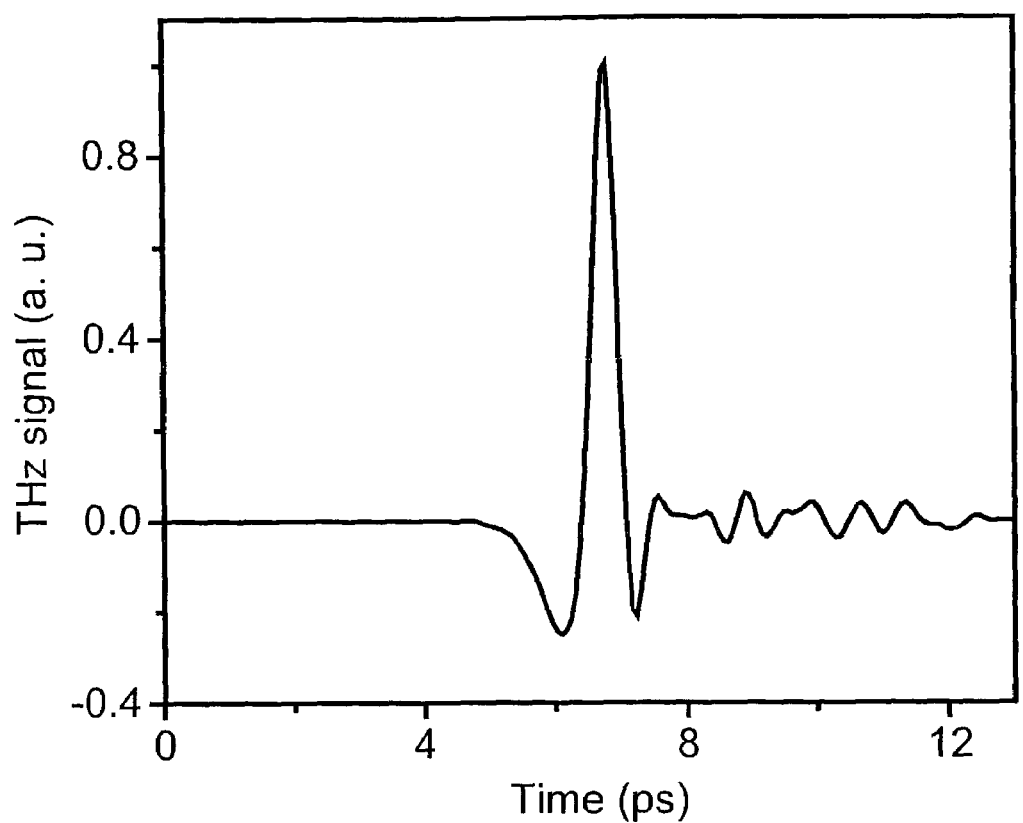
FIG. 12B shows a time domain waveform for the Fourier spectrum shown in FIG. 12A.

This example illustrates Fresnel lens tomographic (FLT) imaging using a broadband pulsed THz wave containing frequency components ranging from 100 GHz to 3 THz, such as the wave depicted in FIGS. 12A and 12B. FIG. 12A shows a Fourier spectrum of an exemplary THz pulse wave form. FIG. 12B shows the time domain wave form corresponding to the Fourier spectrum shown in FIG. 12A.

This example uses an 8-level silicon binary lens with a 30 mm diameter consisting of 14 zones and a focal length of 2.6 cm at 1 THz, having other attributes similar to the lens described above and capable of fabrication and characterization as described above. The imaging system configuration described above and shown in FIG. 5 for the characterization of a THz wave binary lens may be modified for tomographic imaging by inserting an object 25 to be imaged, as shown by dashed lines in FIG. 5, in the radiation path between the THz wave source 34 and binary lens 26. By scanning the time delay between THz pulse 23 and probe beam 20, the temporal waveform at each pixel on the image plane may be measured by using CCD camera 12 to capture the information encoded onto probe beam 20 by EO sensor 24. A Fourier transformation of the temporal waveforms provides the THz field amplitude (or intensity) distribution on the image plane at each frequency. The image of the THz field amplitude at each frequency corresponds to the THz field transmission of a target at certain locations along the z-axis.

Figure 7:
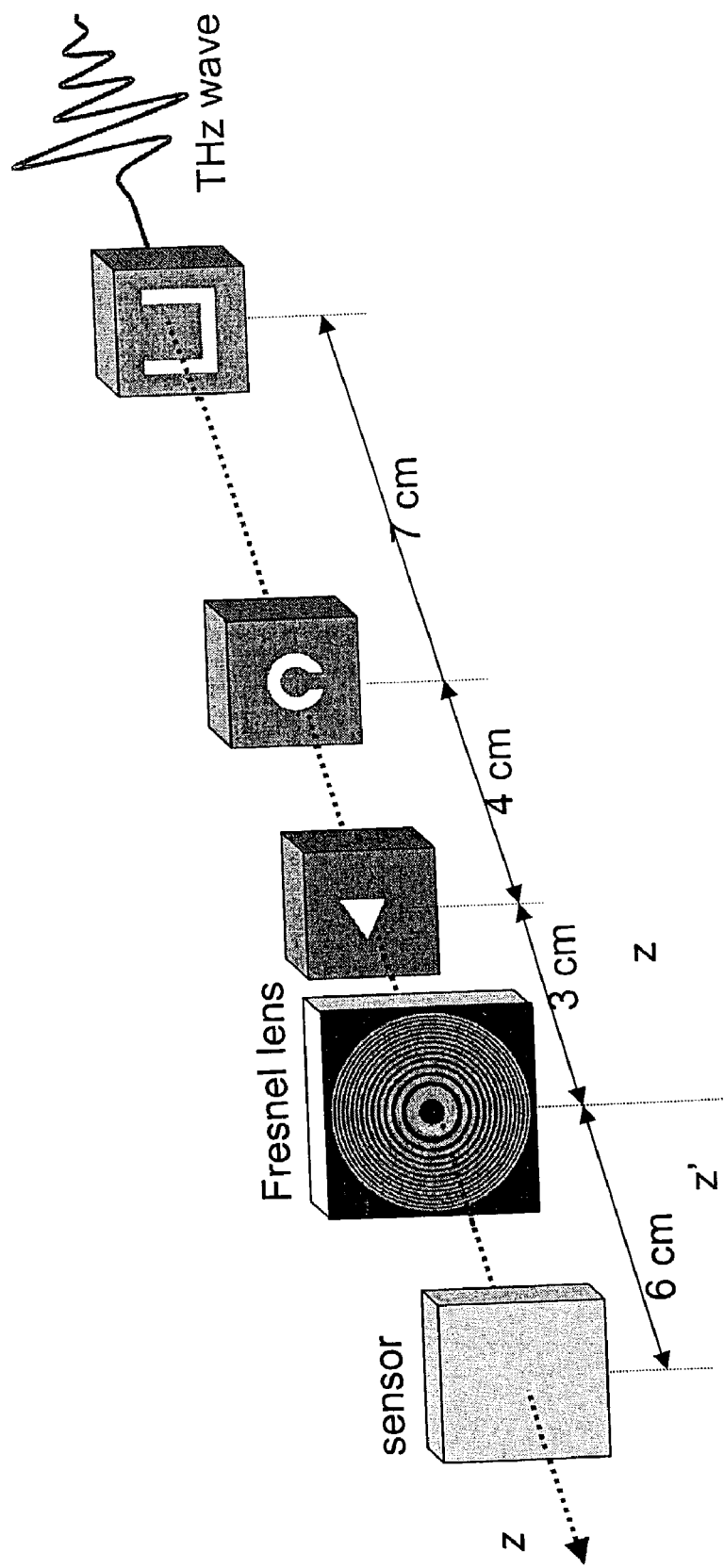
FIG. 7 is a schematic illustration of an exemplary tomographic imaging system using a Fresnel lens to image three plastic sheets cut with patterns of an equilateral triangle (OT), an open circular ring channel (OC), and a square U channel (OU) as shown in FIGS. 8(a), (b), and (c), respectively.

In this example, a target consisting of three plastic sheets cut to form single patterns was imaged. FIG. 7 schematically illustrates the exemplary tomographic imaging arrangement. Three 60 mm×45 mm×2 mm acrylic plastic masks (OU, OC, and OT) with different open patterns shown in FIGS. 8A–8C, respectively, were placed along the THz beam path. Their distances to the lens, corresponding to z in Equation 3, were 3 cm, 7 cm, and 14 cm, respectively. The plastic sheets were transparent to THz frequencies and had a refractive index of 1.5 within the frequency range from 0.5 THz to 2 THz. By scanning the time delay between the THz pulses and the optical probe beam pulses, a temporal waveform of the THz wave at each pixel on the image plane was measured using CCD camera 12. Fourier transformation of the temporal waveforms provided the THz field amplitude (or intensity) distribution on the image plane at each frequency, which formed the image of the THz field transmission of the target.

The measured inverted images of these patterns are shown in FIGS. 8D–8F, respectively. At each frequency, the binary lens imaged a pattern corresponding to a certain depth while images from other patterns remained blurred. The ratio of the measured image size to the actual size of each corresponding pattern agrees well with the theoretical calculation.

Due to the overlap of the targets along the z-axis, each mask's image mixes with the others at certain frequencies. A discriminating image processing algorithm may be used to improve the contrast ratio and suppress unwanted images. For example, an inverse filter can be used to improve the contrast and suppress blurred images from other depths. The inverse filter can be designed according to the imaging system's three-dimensional coherent transfer function (CTF) or optical transfer function as described in Equation 7.

Example 2

Figure 9:
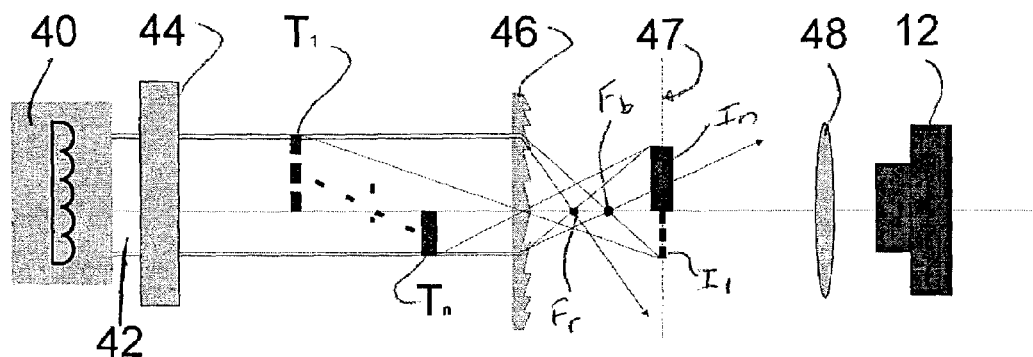
FIG. 9 is a schematic illustration of an exemplary Fresnel tomographic imaging system using a broadband source and a filter placed between the source and the Fresnel lens.

FLT imaging may also be applied to other frequency ranges, such as the visible frequency range. This application requires a relatively larger frequency range in order to obtain a reasonably large imaging depth. FIG. 9 shows an exemplary FLT imaging system for visible light (450 nm to 750 nm wavelength). In FIG. 9, white light source 40 generates white light 42 with a broad wavelength range. White light 42 is directed through an electrically tunable filter (ETF) 44, which is only transparent to the light within a narrow wavelength range of $\lambda_t \pm \delta\lambda_w/2$. The value of $\lambda_t$ can be selected by tuning the ETF. Fresnel lens 46 is used to image a series of targets $T_1$ to $T_n$ onto fixed image plane (FIP) 47. Lens 48 transfers the images $I_1$ and $I_n$ on the fixed image plane to a CCD, a camera, or CCD camera 12. As shown in FIG. 9, $F_r$ is the focal point for red light and $F_b$ is the focal point for blue light.

Using a transmission wavelength window (or band pass) $\delta\lambda_w$ for the ETF of 5 nm, a fixed image distance z' of 200 mm, and a Fresnel lens with the focal length of 100 mm at 600 nm, provides $r_p$=0.346 mm. This gives a depth resolution of 3.3 mm for light at a 450 nm wavelength. At a wavelength of 750 nm, the depth resolution is 2.3 mm. This wavelength-dependent difference in depth resolution is referred to as "color depth resolution." Improvements in depth resolution can be obtained by reducing $\delta\lambda_w$, using a large z', or using a short focal length Fresnel Lens (corresponding to a smaller $r_p$).

Resolution is also limited by the focal depth. With a Fresnel lens having an aperture of 2 cm, the image corresponding to a 450 nm beam has a depth resolution as determined by the focal depth of 1.6 mm. For red light (750 nm), the depth resolution as determined by the focal depth is 0.8 mm. Therefore, the depth resolution mainly depends on the color depth resolution.

Figure 10:
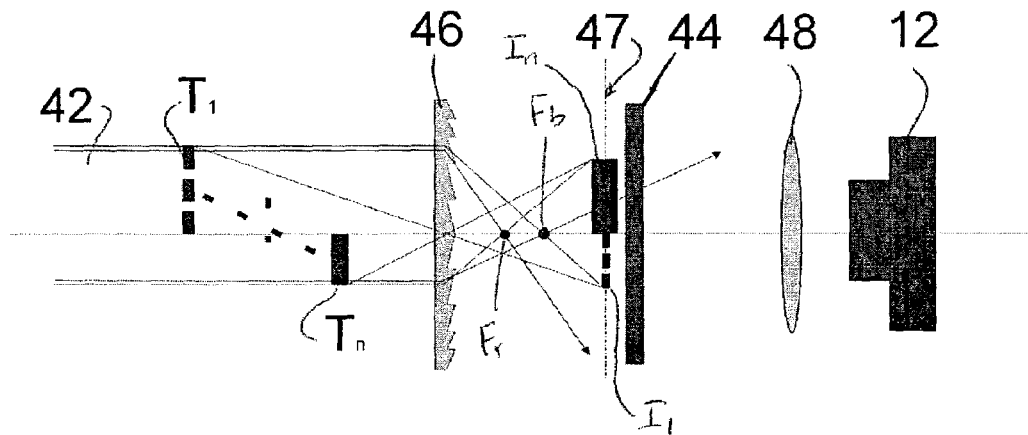
FIG. 10 is a schematic illustration of an exemplary Fresnel tomographic imaging system similar to that of FIG. 9, but with the filter located between the fixed image plane (FIP) and the sensor.

The setup shown in FIG. 9 can be also modified as shown in FIG. 10, if the white light source, including, for example, natural sunlight, is intense enough to create an FLT image. ETF 44 can be put either in front of lens 48 or in front of CCD camera 12. The setup as shown in FIG. 10 is similar to that shown in FIG. 9, except ETF 44 is placed between fixed image plane 47 and lens 48.

ETF 44 is an important element in a visible FLT imaging system. Desirable characteristics for ETF 44 include: random access to any wavelength within its operating range; sufficiently small transmission wavelength window (or band pass); selectable band pass; large aperture; minimal physical thickness; sufficiently short tuning time; insensitivity to polarization; and insensitivity to environmental factors (e.g., ambient temperature and humidity). An exemplary ETF 44 includes a liquid crystal tunable filter (LCTF), an acoustic-optical tunable filter (AOTF), and an interferometer or spectrometer such as a Fabry-Perot Etalon.

A LCTF is built using a stack of polarizers and tunable retardation (birefringent) liquid crystal plates, as is known in the art. The spectral resolution, or band pass, of the LCTF is typically of the order of several nm, although a narrower band pass can also be constructed. LCTF for wavelengths from 400 nm to 800 nm are commercially available.

An AOTF consists of a crystal in which radio frequency (RF) acoustic waves are used to separate a single wavelength of light from a broadband source. The wavelength of light selected is a function of the frequency of the RF applied to the crystal. By varying the frequency, the wavelength of the filtered light can be varied. The common types of AOTFs can operate from the near-UV through the short wave infrared region.

Example 3

Figure 11:
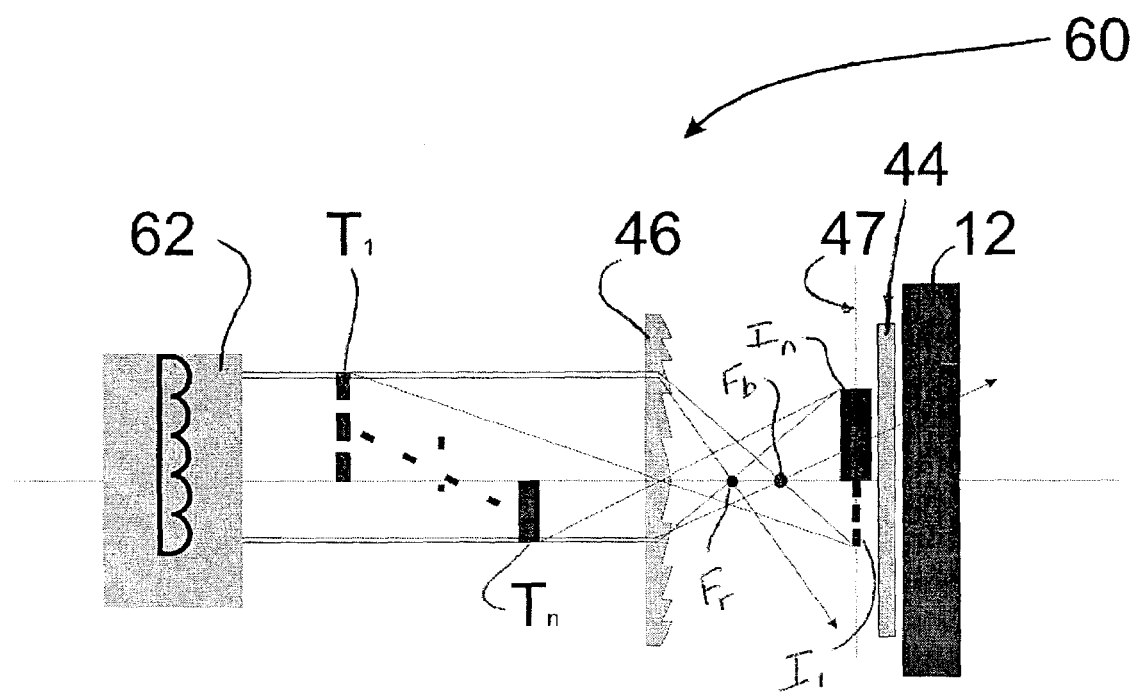
FIG. 11 is a schematic illustration of an exemplary Fresnel tomographic imaging system comprising a tunable narrow-band source and a filter located after the FIP.

FIG. 11 shows a portion of an exemplary FLT imaging setup 60 comprising a frequency tunable THz source (TTS) 62. TTS 62 may be generated, for example, by using a GaSe emitter. A tunable Fabry-Perot filter, for example, may be used for ETF 44. The Image detector may be, for example, a far-infrared CCD camera 12 that measures the THz image using the pyroelectric effect. A similar setup to that shown in FIG. 11 may be used with acoustic waves, using a tunable acoustic wave source.

Time-domain spectroscopy measurement for acoustic waves is known, as described by T. Mast in "Wideband quantitative ultrasonic imaging by time domain diffraction tomography,"J. Acoust. Soc. Am. (1999). Frequency-resolved tomography imaging for acoustic waves using a broadband acoustic pulse source can be obtained in a manner similar to the time-domain method described in Example 1 for THz waves using a broadband source.

CONCLUSION

Thus, an exemplary imaging method comprises aligning a radiation source; a frequency-dependent focal length lens, such as a Fresnel lens; and a sensor in a radiation path with the sensor positioned to capture a frequency-dependent image projected by a lens with a frequency-dependent focal length onto a fixed image plane. The object to be imaged is placed in the path between the radiation source and the lens, and an nth frequency-dependent image of an nth slice of the object along a plane perpendicular to the radiation path is created using radiation at an nth frequency. Thus, for example, a first frequency-dependent image of a first slice of the object along a plane perpendicular to the radiation path is created using radiation at the first frequency, then a second frequency-dependent image of a second slice of the object along a plane perpendicular to the radiation path is created using radiation at the second frequency, and so on. The nth frequency-dependent image is captured with the sensor, for n equal to 1 through m, inclusive, where m equals an integer greater than or equal to 2.

A tomographic image can then be reconstructed by assembling the m frequency-dependent images of the object according to their corresponding magnification factors. The reconstruction of tomographic images using data corresponding to captured images of slices of an object is well-known in the art, and is therefore not discussed in detail. Similarly, the capture and storage of information corresponding to images of slices of an object for use in tomography is also well-known in the art and not discussed in detail. For example, systems for capturing images of slices in the THz frequency range are discussed in International Patent Application No. PCT/US02/36279.

In one FLT imaging embodiment, such as shown in FIGS. 9 through 11, a frequency tunable source or a broadband source with a tunable filter is used to illuminate the object with one narrow band of frequencies at a time, such that each of the nth frequency-dependent images is created in a distinct step. Thus, for example, the three masks as described with respect to Example 1 and shown in FIGS. 7 and 8, may be placed in any of the configurations shown in FIGS. 9 through 11 and the tunable source and/or tunable filter tuned to provide the specific frequency to image each sheet onto the fixed image plane, given the distance of the sheet from the Fresnel lens.

It should be understood that, although the examples use distinct sheets spaced apart from one another, a typical tomographic imaging application comprises imaging of a contiguous object for which the sheets in the above examples represent individual slices of the object. For example, in imaging of a vital organ within a human body, the human body is placed in the radiation path, and the radiation provided at requisite frequencies to image slices of the organ at desired increments from one another. For example, for an organ having a 20 cm length along the z-axis of the radiation path, it may be desired to create a tomographic image using 10 slices of the organ spaced 2 mm apart.

An exemplary Fresnel lens imaging system thus comprises a radiation source, a lens with frequency-dependent focal length, a sensor for capturing frequency-dependent images of the object, and apparatus for facilitating creation and capture of a plurality of frequency-dependent images of the object at a plurality of frequencies. An exemplary Fresnel lens tomographic imaging system further comprises a processor for extracting and assembling the frequency-dependent sectional images of the object to reconstruct the tomographic image of the object. In the embodiment described above with respect to FIGS. 9 and 10, the apparatus for facilitating creation and capture of the plurality of frequency-dependent images comprises a tunable filter for use in conjunction with a broadband source. In another embodiment, the apparatus may comprise a tunable narrowband source. In the embodiment described above with respect to FIG. 11, the apparatus comprises a combination of a tunable source and a tunable filter.

In yet another embodiment, described with respect to FIGS. 5 and 7, the radiation source comprises a broadband THz radiation source and the apparatus for facilitating capture and creation of the plurality of frequency-dependent images comprises components such as a laser source, a splitter, and a THz emitter for generating a THz pulse and an optical probe pulse; an element such as a delay stage for generating a series of time delays between the pump pulse and a probe pulse; and a device such as an EO sensor for modulating the optical probe pulse with the THz pulse. Various apparatus for performing terahertz imaging are discussed in a number of patents, patent applications, and papers of which co-inventor Xi-Cheng Zhang is an inventor or author, including but not limited to U.S. Pat. Nos. 5,952,818 and 6,111,416, incorporated herein by reference. For example, splitters for splitting a laser beam into an optical probe pulse and an optical pump pulse are well-known, as are EO emitters for converting the optical pump pulse into a THz pulse, delay stages for creating a delay between a pump pulse and a probe pulse, EO sensors for modulating the pump pulse with the probe pulse, and various optics for directing, polarizing, splitting, expanding, collimating, and otherwise manipulating optical beams and THz pulses as desired.

The system further comprises apparatus for capturing a temporal waveform at a plurality of pixels on the fixed image plane and a processor for taking a Fourier transform of each temporal waveform to provide a THz field amplitude distribution for each of the plurality of frequencies, where the THz field amplitude distribution comprises the frequency-dependent image for each of the plurality of frequencies. In one embodiment, a CCD camera in combination with the delay stage, pump and probe pulses, EO emitter, and EO detector described above allow capture of the entire temporal waveform for each pixel by the CCD camera. The captured data may be stored in a computer memory, and a programmed computer processor may be used for taking a Fourier transform of the waveform, as is also well-known in the art.

Although discussed with respect to electro-optic THz imaging systems, Fresnel lens THz imaging systems may also be provided using photoconductive antennas for the THz emitter and THz sensor. Similarly, although use of a CCD camera to capture the frequency-dependent images is described, any technology for capturing images known in the art may be used, including but not limited to the use of photosensors and rastering techniques for capturing images a single pixel at a time.

Also, although the imaging methods and systems described are particularly well-suited for tomographic imaging where a desired end result is to compile a computed tomographic image of an object, it should be recognized that the imaging systems and methods described above may be used to create a plurality of frequency-dependent images or even a single frequency-dependent image, without compiling a tomographic image from the plurality of images created.

The methods and systems discussed are particularly well-suited for applications that require imaging targets comprising dielectric materials that are transparent to THz waves, such as powder detection, package inspection, detection of explosive material, and the like. Because a THz wave has a very short wavelength (0.03 mm–1 mm), T-ray tomography can achieve sub-millimeter resolution. T-ray tomography also has potential applications in detecting bacteria, severity of skin burns, and skin cancer. The systems and methods described provide an image modality that can be used to reconstruct any slice of such objects desired to be investigated. Although depicted and described with respect to transmission modes where the sensor receives radiation modified by transmission through the object, it should be understood that reflective modes may also be used in which the sensor receives radiation modified by reflection from the object.

Although the invention is illustrated and described with reference to specific embodiments, the invention is not intended to be limited to the details shown. Rather, various modifications may be made in the details within the scope and range of equivalents of the claims and without departing from the invention.

What is claimed is:

1. A method for tomographic imaging of an object, the method comprising the steps of:
   (a) aligning in a path a radiation source adapted to emit radiation to which the object is essentially transparent, a binary lens having a frequency-dependent focal length, and a sensor for sensing radiation modified by the object, the sensor positioned to capture an image projected by said lens with frequency-dependent focal length onto a fixed image plane;
   wherein said frequency, said lens and said fixed image plane are selected such that:
      i. said lens is positioned substantially perpendicular to said propagation path;
      ii. said fixed image plane is located at a distance z' from said lens along said propagation path also substantially perpendicular to said propagation path and a plane substantially perpendicular to said propagation path at a first distance z from said lens is imaged by said lens on said fixed image plane;
      iii. said frequency $v_i$ is selected such that a plurality of planes $z_i$ along said propagation path imaged on said fixed image plane cover a selected segment along said propagation path sufficient to encompass a desired thickness of an object placed in said radiation path; and
      iv. said binary lens is selected such that:

$z_o = [r_p^2 * z'* v]/[2c\, z' - r_p^2 * v]$ where $r_p^2$ is the lens zone period with the area dimension, c is the speed of light, $z_o$ is the distance of the object from the lens and v is a radiation frequency imaging said object origin on said imaging plane,
   (b) placing the object in the path between the radiation source and the lens at $z=z_o$;
   (c) creating an nth frequency-dependent image of an nth slice of the object in a plane perpendicular to the path using radiation at an nth frequency and capturing the nth frequency-dependent image with the sensor, for n equal to 1 through m, inclusive, where m equals an integer greater than or equal to 2; and (d) reconstructing a 3 dimensional tomographic image of said object by assembling the m frequency-dependent images of the object according to their magnification factors.

2. The method of claim 1 comprising performing step (c) for m frequencies within the THz frequency range.

3. The method of claim 1 comprising performing step (c) for m frequencies within a frequency range selected from the group consisting of visible and audible.

4. The method of claim 1, wherein step (c) comprises a set of sequential steps ($c_n$), each sequential step comprising capturing the frequency-dependent image of the object at only a narrow band of frequencies around the nth frequency.

5. The method of claim 4, wherein each sequential step ($c_n$) further comprises illuminating the object with radiation at only the narrow band of frequencies around the nth frequency.

6. The method of claim 4 comprising placing a tunable filter in the path.

7. The method of claim 6 comprising placing the tunable filter between the fixed image plane and the sensor.

8. The method of claim 6 comprising placing the tunable filter between the radiation source and the object.

9. The method of claim 4, further comprising placing an electrically tunable filter in the path between the fixed image plane and the sensor.

10. The method of claim 1 wherein the radiation source comprises a broadband THz radiation source and step (c) comprises illuminating the object with a THz pulse over a series of time delays between the THz pulse and an optical probe pulse, capturing a temporal waveform of the THz pulse as transmitted through the object at a plurality of pixels on the fixed image plane, and taking a Fourier transform of each temporal waveform to provide a THz field amplitude distribution on the fixed image plane for each of the m frequencies, the THz field amplitude distribution comprising the frequency-dependent image for each of the m frequencies.

11. The method of claim 10, wherein the sensor comprises an electro-optic crystal for modulating the optical probe pulse with the THz pulse, thereby creating a modulated optical probe pulse, the method comprising capturing the temporal waveform using a charge coupled device to detect the modulated optical probe pulse.

12. The method according to claim 1 wherein said radiation is THz frequency radiation and said image is created on said image plane as a convolution of a plurality of 2d slices each at a different position z along the propagation path and the image field distribution $U_f(X_f, Y_{ou}, Z_o)$ is described by:

$$|U_i(x_i, y_i, z')| \propto$$
$$\left| \int \int \int o(x_o, y_o, z_0) \exp[ik(z_o - z')] h(x_o + Mx_i, y_o + My_i, z_o - M^2 z') \, dx_o dy_o dz_o \right|$$

where:
$O(X_o, Y_o, Z_o)$ is the object function,
$M = -z'/z$ is the magnification factor, and the Fourier transform of h(x,y,z) is the THz imaging system's three-dimensional coherent transfer function used to reconstruct the 3d image of the object.

13. A system for constructing a plurality of sectional images of a solid object, the system comprising:

a radiation source adapted to emit radiation to which the object is essentially transparent at a plurality of frequencies in a radiation path directed at the object;

a binary lens with frequency-dependent focal length adapted to receive radiation propagating along a propagation path and modified by the object and to project onto a fixed image plane a frequency-dependent image of a slice of the object perpendicular to the radiation path;

a sensor for capturing the frequency-dependent image of the object;

means for facilitating creation and capture of a plurality of frequency-dependent images of the object at a plurality of frequencies and wherein:

i. Said lens is positioned substantially perpendicular to said propagation path;

ii. said fixed image plane is located at a distance z' from said lens along said propagation path also substantially perpendicular to said propagation path and a plane substantially perpendicular to said propagation path at a first distance z from said lens is imaged by said lens on said fixed image plane;

iii. said plurality of frequencies $v_i$ is selected such that a plurality of planes $z_i$ along said propagation path imaged on said fixed image plane cover a selected segment along said propagation path sufficient to encompass a desired thickness of an object placed in said radiation path; and iv. said binary lens satisfies the equation:

$$z_o = [r_p^2 * z'^* v]/[2c\, z' - r_p^2 * v]$$

where $r_p^2$ is the lens zone period with the area dimension, c is the speed of light, $z_o$ is the distance of the object from the lens and v is a radiation frequency imaging said object origin on said imaging plane.

14. The system of claim 13 further comprising means for assembling the plurality of frequency-dependent images of the object according to their magnification factors to reconstruct the tomographic image of the object.

15. The system of claim 14, wherein the means for facilitating creation and capture of a plurality of frequency-dependent images comprises a tunable radiation source.

16. The system of claim 15, wherein the means for facilitating creation and capture of a plurality of frequency-dependent images further comprises a tunable filter placed in the radiation path.

17. The system of claim 13, wherein the frequency-dependent focal length lens comprises a Fresnel lens.

18. The system of claim 13, wherein the sensor comprises a charge coupled device.

19. The system of claim 13, wherein the means for facilitating creation and capture of a plurality of frequency-dependent images comprises a broadband radiation source and a tunable filter placed in the radiation path.

20. The system of claim 19, wherein the tunable filter is placed in the radiation path between the radiation source and the object.

21. The system of claim 19, wherein the tunable filter is placed in the radiation path between the fixed image plane and the sensor.

22. The system of claim 19, wherein the tunable filter comprises an electrically tunable filter.

23. The system of claim 22, wherein the electrically tunable filter comprises a filter selected from the group consisting of: a liquid crystal tunable filter, an acoustic-optical tunable filter, an interferometer, and a spectrometer.

24. The system of claim 22, wherein the electrically tunable filter comprises a Fabry-Perot Etalon.

25. The system of claim 16, wherein the radiation source comprises a tunable terahertz source and the tunable filter further comprises a Fabry-Perot Etalon.

26. The system of claim 19, wherein the radiation source comprises a white light source and the tunable filter comprises an electrically tunable filter.

27. The system of claim 13 wherein the radiation source comprises a broadband THz radiation source and the system further comprises:
   means for generating a THz pulse and an optical probe pulse;
   means for generating a series of time delays between the THz pulse and the optical probe pulse;
   means for modulating the optical probe pulse with the THz pulse after the THz pulse has been modified by the object;
   means for capturing a temporal waveform corresponding to the modulated optical pulse at each of a plurality of pixels on the fixed image plane; and
   means for taking a Fourier transform of each temporal waveform to provide a THz field amplitude distribution for each of the plurality of frequencies, the THz field amplitude distribution on the fixed image plane at each frequency comprising the frequency-dependent image for each of the plurality of frequencies.

28. The system of claim 27 further comprising:
   a first set of optics for expanding and collimating the probe pulse; and
   a second set of optics for expanding and collimating the pump pulse.

29. The system of claim 13 wherein the radiation source comprises a broadband THz radiation source and the system further comprises:
   a source for generating an optical beam;
   a splitter for splitting the optical beam into an optical pump pulse and an optical probe pulse;
   a delay stage for generating a series of time delays between the optical pump pulse and the optical probe pulse;
   an EO emitter for converting the optical pump pulse into a THz pulse;
   an EO sensor for modulating the optical probe pulse with the THz pulse as modified by the object;
   a charge coupled device for capturing the modulated probe pulse at a plurality of pixels on the fixed image plane at a plurality of delay times between the pump pulse and the probe pulse to enable characterization of a complete temporal waveform for the THz pulse for each pixel; and
   a processor for taking a Fourier transform of each temporal waveform to provide a THz field amplitude distribution for each of the plurality of frequencies, the THz field amplitude distribution on the fixed image plane at each frequency comprising the frequency-dependent image for each of the plurality of frequencies.

30. The system according to claim 13 wherein said binary lens comprises at least 8 levels L.

31. The system according to claim 30 wherein said binary lens has been etched to a depth of $\lambda/L(n_{THz}-1)$.

32. A system for constructing a plurality of images of a solid object, the system comprising:
   a radiation source and related optics for generating an expanded optical pump pulse and an expanded optical probe pulse with a series of time delays between the optical pump pulse and the optical probe pulse;
   a THz emitter for converting the optical pump pulse into a broadband THz pulse directed at the object;
   a binary lens with a frequency-dependent focal length adapted to receive the THz pulse as modified by the object and to project onto a fixed image plane a frequency-dependent image of a slice of the object perpendicular to the radiation path;
   a THz sensor on the fixed image plane for modulating the optical probe pulse with the THz pulse as modified by the object to capture the frequency-dependent image of the object;
   a charge coupled device for capturing the modulated probe pulse at a plurality of pixels on the fixed image plane at a plurality of delay times between the pump pulse and the probe pulse to enable characterization of a complete temporal waveform for the THz pulse for each pixel;
   a processor for taking a Fourier transform of each temporal waveform to provide a THz field amplitude distribution for each of the plurality of frequencies, the THz field amplitude distribution on the fixed image plane at each frequency comprising the frequency-dependent image for each of the plurality of frequencies wherein:
   i. said THz pulse propagates along a propagation path;
   ii. said lens is positioned substantially perpendicular to said THz pulse propagation path;
   iii. said fixed image plane is located at a distance z' from said lens along said THz pulse propagation path also substantially perpendicular to said propagation path and a plane substantially perpendicular to said propagation path at a first distance z from said lens is imaged by said lens on said fixed image plane;
   iv. said plurality of frequencies $v_i$ is selected such that a plurality of planes $z_i$ along said propagation path imaged on said fixed image plane cover a selected segment along said propagation path sufficient to encompass a desired thickness of an object placed in said radiation path; and
   v. said binary lens is satisfies the equation:

$$z_o = [r_p^2 * z'^* v]/[2c\, z' - r_p^2 * v]$$

where $r_p^2$ is the lens zone period with the area dimension, c is the speed of light, $z_o$ is the distance of the object from the lens and v is a radiation frequency imaging said object origin on said imaging plane.

33. A method for generating a three dimensional image of a stationary object by illuminating said object with radiation to which the object is transparent and projecting with a frequency dependent binary lens a plurality of two dimensional images of said object on a fixed imaging plane, the two dimensional images representing a plurality of parallel two dimensional cross sections of said object, the method comprising:
   (a) determining the relationship between z as a function of a plurality of radiation frequencies v for different fixed image plane distances z' wherein z is a distance of an object plane from said binary lens where said plane is focussed on said image plane and selecting a radiation frequency range and a fixed image distance sufficient to image on said fixed image plane said plurality of two dimensional object cross sections;

(b) for a selected z, determine a Fresnel zone period for said binary lens such that $$z' = -r_p^2/2\lambda$$

(c) establishing a radiation path for said radiation and placing said binary lens and said imaging plane in said path in the positions selected in step (a);

(d) placing said object in said radiation path in said radiation path ahead of said binary lens selected according to step (c) at a distance such that for the selected radiation frequency range said plurality of two dimensional object cross sections are all imaged on said fixed imaging plane;

(e) detecting an image plane distribution field of said object $$|U_i(x_i, y_i, z')| \propto$$
$$\left| \int \int \int o(x_o, y_o, z_0) \exp[ik(z_o - z')] h(x_o + Mx_i, y_o + My_i, z_o - M^2 z') \, dx_o dy_o dz_o \right|$$

where:

$O(X_o, Y_o, Z_o)$ is the object function,
$M = -z'/z$ is the magnification factor,
and the Fourier transform of $h(x,y,z)$ is the THz imaging system's three-dimensional coherent transfer function used to reconstruct the 3d image of the object; and (f) reconstructing said 3 dimensional tomographic image of said object by assembling the plurality of said two-dimensional images into a three dimensional image according to their magnification factors.

34. The method of claim 33, wherein the object comprises a dielectric material and the method further comprises using the tomographic image of the object for detection of powders, package inspection, detection of explosive materials, evaluation of skin burns, detection of skin cancer, and detection of bacteria.

35. The method of claim 33, wherein the tomographic image has sub-millimeter resolution.

36. The method of claim 33, wherein the radiation source comprises a broadband THz radiation source and the method further comprises the steps of:
   (i) generating a THz pulse and an optical probe pulse;
   (ii) generating a series of time delays between the THz pulse and the optical probe pulse;
   (iii) modulating the optical probe pulse with the THz pulse after the THz pulse has been modified by the object;
   (iv) capturing a temporal waveform corresponding to the modulated optical pulse at each of a plurality of pixels on the fixed image plane; and
   (v) taking a Fourier transform of each temporal waveform to provide a THz field amplitude distribution for each of the plurality of frequencies, the THz field amplitude distribution on the fixed image plane at each frequency comprising the frequency-dependent image for each of the plurality of frequencies.

37. The method of claim 33 wherein the radiation source comprises a broadband THz radiation source and the method further comprises:
   (i) a step for directing a THz pulse at the object;
   (ii) a step for capturing a temporal waveform at each of a plurality of pixels on the fixed image plane corresponding to the THz pulse as modified by the object; and
   (iii) a step for taking a Fourier transform of each temporal waveform to provide a THz field amplitude distribution for each of the plurality of frequencies, the THz field amplitude distribution on the fixed image plane at each frequency comprising the frequency-dependent image for each of the plurality of frequencies.

* * * * *